United States Patent [19]
Goto et al.

[11] Patent Number: 4,695,572
[45] Date of Patent: Sep. 22, 1987

[54] ISOINDOLINONE DERIVATIVES, PRODUCTION AND USE THEREOF

[75] Inventors: Giichi Goto, Toyono; Yoshiaki Saji, Kawanishi, both of Japan

[73] Assignee: Takeda Chemical Industries, Ltd., Osaka, Japan

[21] Appl. No.: 774,470

[22] Filed: Sep. 10, 1985

[30] Foreign Application Priority Data

Sep. 14, 1984 [JP] Japan .................. 59-193073

[51] Int. Cl.$^4$ .................. A61K 31/40; C07D 209/46
[52] U.S. Cl. .................. 514/278; 546/19; 546/122; 546/200
[58] Field of Search .................. 546/19; 514/278

[56] References Cited

U.S. PATENT DOCUMENTS 3,966,931 6/1976 Jeanmart et al. .................. 514/253

FOREIGN PATENT DOCUMENTS 0091241 10/1983 European Pat. Off. .
1358680 7/1974 United Kingdom .

Primary Examiner—Joseph Paul Brust
Attorney, Agent, or Firm—Wegner & Bretschneider

[57] ABSTRACT

A compound of the formula

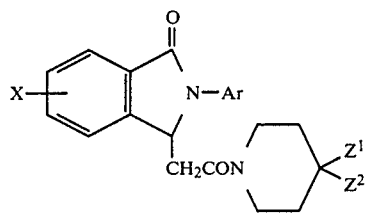

wherein X is hydrogen, halogen or nitro; Ar is phenyl or naphthyridinyl which may optionally be substituted; and either one of $Z^1$ and $Z^2$ is hydrogen and the other is lower alkanoyloxy or hydroxy, each of $Z^1$ and $Z^2$ is lower alkoxy, or $Z^1$ and $Z^2$ combinedly represent hydroxyimino, oxo or a group of the formula:

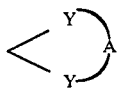

in which Y is oxygen or sulfur and A is a branched or unbranched lower alkylene chain; and a salt thereof, act on the central nervous system but are weak in adverse effects such as hypnotic and muscle relaxant effects.

14 Claims, No Drawings

ISOINDOLINONE DERIVATIVES, PRODUCTION AND USE THEREOF

As far as isoindolinone derivatives are concerned, there are already a number of relevant reports (e.g. South African Pat. Nos. 7208795 and 7309139. European Patent publication (laid open) 0091241.

Whereas CNS drugs, inclusive of antianxiety drugs, are required, for example, to be orally administrable and free of adverse effects such as muscle relaxant effect. Compounds which are satisfactory from this viewpoint have not yet been found.

This invention provides compounds of the formula

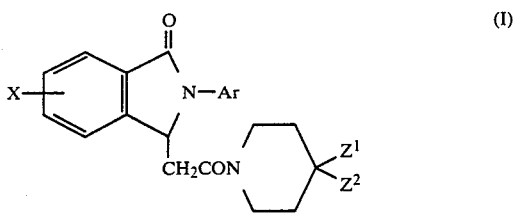

wherein X is hydrogen, halogen or nitro; Ar is a phenyl or naphthyridinyl which may optionally be substituted, and either one of $Z^1$ and $Z^2$ is hydrogen and the other is lower alkanoyloxy or hydroxy, each of $Z^1$ and $Z^2$ is lower alkoxy, or $Z^1$ and $Z^2$ combinedly represent hydroxyimino, oxo or a group of the formula:

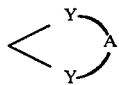

in which Y is oxygen or sulfur and A is a branched or unbranched lower alkylene chain; and a salt thereof, which act on the central nervous system and are useful, in particular, as antianxiety drugs.

Referring to X in the above formula (I), the halogen represented by X includes fluorine, chlorine, bromine and iodine and preferably chlorine, and X is preferably hydrogen.

The phenyl or naphthyridinyl represented by Ar may have one or two substituents and such substituents include, among others, halogen (e.g. fluorine, chlorine, bromine, iodine), hydroxy, lower ($C_{1-4}$) alkyl (e.g. methyl, ethyl, propyl, isopropyl, butyl), lower ($C_{1-4}$) alkoxy (e.g. methoxy, ethoxy, propoxy, isopropoxy, butoxy), nitro, amino, methylenedioxy, phenoxy, benzyloxy, lower ($C_{2-5}$) alkanoyloxy (e.g. acetoxy, propionyloxy, butyryloxy), α- or ω-hydroxylower ($C_{1-4}$) alkyl (e.g. hydroxymethyl, 2-hydroxyethyl), benzoyl, amido, cyano, trifluoromethyl, lower ($C_{1-4}$) alkylthio (e.g. methylthio, ethylthio, propylthio, butylthio), lower ($C_{2-5}$) alkanoyloxy-lower ($C_{1-3}$) alkyl (e.g. acetyloxymethyl, acetyloxyethyl, propionyloxymethyl), lower ($C_{2-5}$) alkanoylamino (e.g. acetylamino, propionylamino) and alkoxycarbonyl (e.g. methoxycarbonyl, ethoxycarbonyl, butoxycarbonyl, isopropoxycarbonyl, propoxycarbonyl).

The above-mentioned substituent or substituents may be located at any position or positions on the benzene or naphthyridine ring. Preferred are those compounds which have such a substituent, preferably lower alkoxy, at position 4 of the benzene ring or a substituent, preferably halogen or lower alkyl, at position 5 or 7 of a naphtyridine ring, for example the 1,8-naphthyridine ring.

The 1,8-naphthyridine is preferably bonded to N at position 2 thereof.

Ar is preferably a naphthyridinyl group, in particular a 7-halogen substituted-1,8-naphthyridinyl group.

Referring to $Z^1$ and $Z^2$, the lower ($C_{1-4}$) alkanoyloxy is, for example, formyloxy, acetoxy, propionyloxy, isopropionyloxy or butyryloxy, and the lower ($C_{1-4}$) alkoxy is, for example, methoxy, ethoxy, propoxy or isopropoxy.

When $Z^1$ and $Z^2$ combinedly represent a group of the formula

Y is preferably oxygen and the lower alkylene chain represented by A is preferably of $C_{2-4}$ and may have one or more lower ($C_{1-4}$) alkyl side chains (e.g. methyl, ethyl, propyl, isopropyl, butyl). In particular, it is preferable that $Z^1$ and $Z^2$ form ethylenedioxy.

When they are basic, the compounds (I) according to the invention may be in the form of acid addition salts, in particular in the form of physiologically acceptable acid addition salts, such as salts with inorganic acids (e.g. hydrochloric acid, nitric acid, phosphoric acid, hydrobromic acid) or with organic acids (e.g. acetic acid, propionic acid, fumaric acid, maleic acid, tartaric acid, citric acid, malic acid, oxalic acid, benzoic acid, methanesulfonic acid, benzenesulfonic acid).

The compounds (I) can be produced, for example, by subjecting to a condensation reaction a compound of the formula

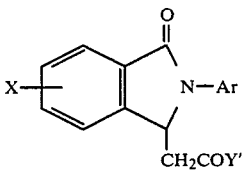

wherein X and Ar are as defined above and Y' is a hydroxyl group or a reactive derivative thereof and a compound of the formula

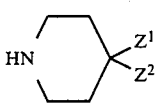

wherein $Z^1$ and $Z^2$ are as defined above.

Referring to the compound (II), Y', when it is a reactive derivative of hydroxy, is, for example, halogen (e.g. fluorine, chlorine, bromine, iodine; preferably chlorine or bromine), lower ($C_{1-4}$) alkoxy (e.g. methoxy, ethoxy, propoxy, isopropoxy, butoxy) or a N-hydroxydiacylimide ester (e.g. N-hydroxysuccinimide ester, N-hydroxyphthalimide ester, N-hydroxy-5-norbornene-2,3-dicarboximide ester).

That compound in which Y' is halogen, namely an acid halide, can be produced by halogenating that compound in which Y' is hydroxy, namely a carboxylic acid, by a per se known method, for example by treating with a halogenating agent (e.g. phosphorus oxychloride, phosphorus oxybromide, phosphorus pentachloride, phosphorus pentabromide, phosphorus trichloride, phosphorus tribromide, thionyl chloride, thionyl bromide, sulfuryl chloride, oxalyl chloride, cyanuric chloride, boron tribromide, hydrogen iodide).

The solvent to be used in halogenation may be any solvent which is in common use. Chloroform, dichloromethane, dichloroethane, benzene and toluene are preferred examples.

The reaction of compound (II) and compound (III) is carried out by a per se known method. For instance, the compound (I) can be produced by deriving a compound (II: Y'=hydroxy) to a compound (II: Y'=halogen) by a per se known method, and then reacting the latter with a compound (III), by reacting a compound (II: Y'=hydroxy) as it is with a compound (III) in the presence of an acid activating agent such as carbonyldiimidazole, dicyclohexylcarbodiimide, diethyl phosphorocyanidate or diphenylphosphoryl azide, or by reacting a compound (II: Y'=lower alkoxy) directly with a compound (III). In each case, the reaction can generally be effected in an organic solvent such as a hydrocarbon solvent (e.g. pentane, hexane, benzene, toluene), a halogenated hydrocarbon solvent (e.g. dichloromethane, chloroform, dichloroethane, carbon tetrachloride), an ether solvent (e.g. ethyl ether, tetrahydrofuran, dioxane, dimethoxyethane), an ester solvent (e.g. ethyl acetate, butyl acetate, ethyl propionate), an amide solvent (e.g. dimethylformamide, dimethylacetamide, hexamethylphosphoramide) or dimethyl sulfoxide, with cooling ($-10°$ C. to $10°$ C.), at room temperature ($11°$ C. to $40°$ C.) or with heating ($41°$ C. to $120°$ C.). The reaction time is generally 10 minutes to 12 hours. The compound (III) is preferably used in an amount of 1.0 to 3.0 equivalents based on the compound (II). If necessary, the reaction is conducted in the presence of an organic base such as pyridine, 4-dimethylaminopyridine, triethylamine, diisopropylamine, triethylenediamine or tetramethylethylenediamine, or inorganic base such as sodium hydrogen carbonate, potassium hydrogen carbonate, sodium carbonate, potassium carbonate, sodium hydroxide or potassium hydroxide.

When the reactive derivative of the above compound (II: Y'=hydroxy) is an N-hydroxydiacylimide ester, the reaction of such reactive derivative and the compound (III) is generally carried out in a solvent such as dichloromethane, tetrahydrofuran, chloroform, dimethylformamide, acetonitrile or water. Any other solvents inert to the reaction may also be used. The reaction is performed, if desired, in the presence of an organic amine base or inorganic base as mentioned above. The reaction temperature is generally $-10°$ C. to $100°$ C., preferably $0°$ C. to $30°$ C.

As far as the compound (II) is concerned, such compound in which Y' is hydroxy can readily be obtained by hydrolyzing the corresponding ester in which Y' is lower alkoxy by a per se known method, for example by treatment with an alkali metal hydroxide (e.g. sodium hydroxide, lithium hydroxide, potassium hydroxide), an alkali metal carbonate (e.g. potassium carbonate, sodium carbonate, lithium carbonate), an inorganic acid (e.g. hydrochloric acid, sulfuric acid, nitric acid, phosphoric acid, hydroiodic acid) or an organic acid (e.g. acetic acid, propionic acid, trifluoroacetic acid, monochloroacetic acid, trichloroacetic acid, methanesulfonic acid, toluenesulfonic acid). Any solvent which is generally usable may be used as the solvent in conducting the hydrolysis. Water, lower ($C_{1-4}$) alkanols (e.g. methanol, ethanol, propanol, butanol), dioxane and dimethylformamide are preferred examples. When an organic acid is used, particular use of a solvent is not always needed. The reaction is conducted generally at a temperature of about $-5°$ C. to about $120°$ C., preferably $0°$ C. to $80°$ C.

The compound (II: Y'=lower alkoxy) can be produced by the following reactions:

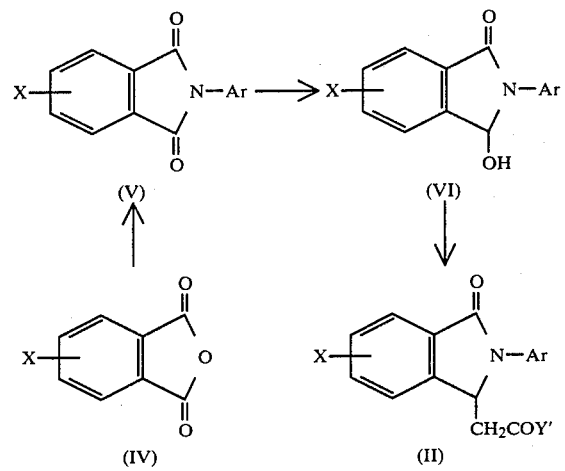

In the above formulas, X, Ar and Y' are as defined above.

The starting compound of general formula (VI) can be produced according to the method described in J. Org. Chem., 26, 2273 (1961) or in Chem. Commun., 245 (1968). Thus, for example, the compound (VI) can be produced easily by first producing a compound (V) by reaction of a compound (IV) with an amine of the formula

Ar—NH$_2$     (VII)

wherein Ar is as defined above by the method described in Chem. Ber., 40, 4850 (1907), Bull. Soc. Chim. France, 26, 749 (1959), Il Farmaco Ed. Sc., 23, 448 (1968) or Arzneim.Forsch., 12, 1207 (1962) or a modification thereof and then follows the procedure described in J. Org. Chem., 26, 2273 (1961) or Chem. Commun., 245 (1968).

The compound (II: Y'=lower alkoxy) can be produced by reacting the compound (VI) with a compound of the formula

Ph$_3$P=CHCOY'     (VIII)

wherein Y' is lower alkoxy. The reaction of compound (VI) and compound (VIII) is carried out in an organic solvent such as toluene, benzene, xylene, ethyl acetate, dimethoxyethane or dichloromethane. Any other organic solvent which will not disturb the reaction may also be used. The reaction is conducted generally at a temperature of about $10°$ C. to about $160°$ C., preferably $25°$ C. to $120°$ C., for about 10 minutes to about 12 hours, preferably 30 minutes to 2 hours.

The compound (III) can be produced easily by a per se known method (Tetrahedron, 27, 411 (1971), J. Chem. Soc., (B), 1087 (1971) or J. Chem. Soc., (B), 127 (1970)) or a modification thereof.

For each compound (I) according to the invention, there exist optical isomers, and these isomers and the racemic modification all fall within the scope of the present invention. The compound (I) according to the invention is generally obtained in the racemic form. The respective optical isomers can be obtained as necessary by optical resolution according to a per se known method. It is also possible, for example, to produce the compound (I) in an optically active form by first subjecting the compound (II: Y'=hydroxy) to optical resolution by a per se known method and then reacting the thus-obtained optically active (II) with a compound (III) according to the above-mentioned method. As resolving agents usable for the compound (II: Y'=hydroxy), there may be mentioned, for example, optically active amines such as cinchonine, brucine, quinine and amino acids.

The compounds (I) according to the invention act on the central nervous system of mammals. Having strong specific binding activity to benzodiazepine receptors, they show strong and lasting antianxiety activity in the anticonflict test in rats. The minimum lethal doses (MLDs) for the compounds of the invention are not less than 1,000 mg/kg (p.o.) in rats, hence very large as compared with minimum effective doses (MEDs) thereof, so that the safety margins for said compounds are very broad. For the compound (I: Ar=7-chloro-1,8-naphthyridin-2-yl), for instance, the MED for the above-mentioned antianxiety activity in rats is not higher than 20 mg/kg (p.o.).

As compared with the known isoindolinone derivatives mentioned above or those benzodiazepine drugs which are currently on the market as antianxiety drugs, the compounds (I) of the invention are broader in safety margin, very good in distinctness of their activity or activities from the hypnotic, muscle relaxant or like activity as a side effect, and very weak or slight in activity to produce such adverse effects as drowsiness and dizziness. Even peroral administration of said compounds can produce remarkable therapeutic effects. Therefore, said compounds are useful as antianxiety drugs for mammals, inclusive of humans.

As diseases to be treated with the compounds of the invention, there may be mentioned various psychosomatic diseases and anxiety neuroses, such as autonomic imbalance, neurotic emesis neurodermatitis, alopecia areata, angina pectoris nervosa and dyspnoeneurosis, and said compound can be used in the prevention or treatment of such diseases. The compounds according to the invention also have anticonvulsant activity. Therefore, they can also be used in the treatment of epilepsy or traumatic convulsion.

The compounds of the invention are administered to mammals, inclusive of humans, in the dosage form of tablets, granules, capsules, injections, suppositories and so forth. The dose varies depending on the disease to be treated, symptoms thereof and other factors. Generally, however, the oral dose for adult humans is 0.01 mg to 200 mg, preferably 0.1 mg to 20 mg, per day.

[Biochemical Test Example]

The compounds (I) according to the invention were tested for their affinity for benzodiazepine receptors using radioactive [$^3$H]-diazepam.

The assay for specific binding to benzodiazepine receptors was performed according to the method described in the literature (Nature, 266, 732 (1977); European J. Pharmacol., 48, 263 (1978)). Thus, a crude mitochondrial fraction obtained from the cerebral cortex of SD strain male rats aged 9 to 10 weeks was suspended in B=mM Tris-HCl buffer (pH 7.4), followed by addition of the test drug at several concentration levels and of [$^3$H]diazepam (final concentration 2 nM). Each suspension was incubated at 4° C. for 20 minutes and then filtered through a Whatman GF/B glassfiber filter, and the radioactivity of [$^3$H]diazepam on the filter was measured with a liquid scintillation counter. In this manner, the $IC_{50}$ value, namely the concentration of the test drug at which the [$^3$H]diazepam binding was inhibited by 50%, was determined.

The results obtained are shown in Table 1.

| compound (I) X | Ar | $Z^1, Z^2$ | $IC_{50}$ [nM] |
| --- | --- | --- | --- |
| 5-Cl | 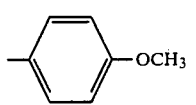 | =NOH | 3.47 |
| 5-Cl | " | =O | 2.40 |
| 5-NO$_2$ | " | 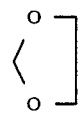 | 21.9 |
| 5-Cl | " | 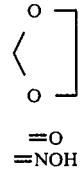 | 8.71 |
| 5-NO$_2$ | " | =O | 6.16 |
| 5-NO$_2$ | " | =NOH | 7.94 |
| H | 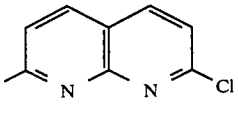 | =O | 0.537 |
| H | " | 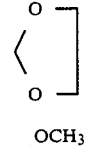 | 0.380 |
| H | " |  | 1.29 |
| H | " | =NOH | 0.645 |
| H | " | 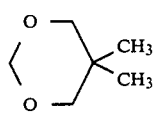 | 2.40 |
| H | " | 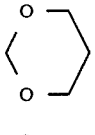 | 4.90 |
| H | " | 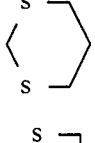 | 0.562 |
| H | " | 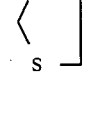 | 1.23 |

| compound (I) X | Ar | $Z^1, Z^2$ | $IC_{50}$ [nM] |
|---|---|---|---|
| H | " | OCOCH₃ / H | 0.501 |
| H | " | OCOC₂H₅ / H | 1.00 |
| H | " | OH / H | 0.794 |

[Pharmacological Test Example]

The compounds (I) of the invention were examined for antianxiety, muscle relaxant and sleep-inducing activities.

(1) Antianxiety activity

The antianxiety activity measurement was performed in accordance with Vogel et al. [Psychopharmacologia, 21, 1 (1970)] as follows: An apparatus comprising a large clear box with a stainless steel grid floor and a smaller opaque dark box provided with a drinking tube was arranged such that a rat placed therein could receive, on the sole, electric shocks through the grid floor following each twentieth lick. The test compound was orally administered to each male rat (SD/JCL) deprived of water for 48 hours prior to the test, which rat was then 30, 60 or 180 minutes after administration, placed in the apparatus mentioned above and the number of licks was recorded over 3 minutes. The increase in the number of licks as compared with a physiological saline group was determined and taken as a measure of antianxiety potency, and the minimum effective dose determined accordingly.

(2) Muscle relaxant activity

Groups of 6 rats were used. The rats were placed on a rotating rod with a diameter of 3.5 cm. The rod rotated with a speed of 8 revolutions per minute. The animals were observed for whether they fell off the rod within 1 minute or not. The dose, $ED_{50}$, of the test compound as required to make 50% of the rats fall off the rod was calculated [J. Am. Pharmaceutical Association, 46, 208 (1957)].

(3) Sleep-inducing activity

Mice, in groups of eight, were orally administered the test compound and, 30 minutes later, intraperitoneally administered 25 mg/kg of pentobarbital. The loss of righting reflex which lasted for 2 minutes or longer during the 30-minute period following pentobarbital administration was taken as an indication of sleep potentiation. The dose, $ED_{50}$, of the test compound as required to achieve sleep potentiation in 50% of mice was calculated.

The antianxiety, muscle relaxant and sleep-inducing activities of three typical examples of the compound (I) are shown in Table 2.

TABLE 2

| Compound (I) | | | Antianxiety activity MED (mg/kg) | Muscle relaxant activity $ED_{50}$ (mg/kg) | Sleep-inducing activity $ED_{50}$ (mg/kg) |
|---|---|---|---|---|---|
| X | Ar | $Z^1, Z^2$ | | | |
| H |  | O–⟨ / O– | 5 | >80 | >50 |
| H | " | =O | 20 | >80 | 24.8 |
| H | " | OCH₃ / OCH₃ | <20 | >40 | ≈50 |
| H | " | H / OH | >20 | >80 | 40.2 |

EXAMPLE

The following examples are intended to illustrate this invention in further detail and should by no means be construed as limiting the scope of the invention.

EXAMPLE 1

5-Chloro-3-(1,4-dioxa-8-azaspiro[4.5]decan-8-yl)carbonylmethyl-2-(4-methoxyphenyl)isoindolin-1-one With ice-cooling and stirring, 1.57 g of 1,4-dioxa-8-azaspiro[4.5]decane, 2.3 ml of triethylamine and 2.12 g of diethyl phosphorocyanidate were successively added to a solution of 3.32 g of 6-chloro-2-(4-methoxyphenyl)-3-oxoisoindoline-1-acetic acid in 30 ml of dimethylformamide. The mixture was stirred with ice-cooling for an hour. To the reaction mixture was added 150 ml of ice water and the mixture was allowed to stand to give a crystalline precipitate, which was collected by filtration, washed with water and dried. Recrystallization from ether gave 4.13 g of colorless crystals melting at 156°–157° C.

Elemental analysis: Calcd. for $C_{24}H_{25}ClN_2O_5$: C 63.08; H 5.52; N 6.13 Found: C 63.26; H 5.54; N 5.92.

EXAMPLE 2

In the same manner as Example 1, there were obtained the compounds listed in Table 3.

TABLE 3

[Structure: isoindolin-1-one with X substituent on benzene ring, N-substituted with 4-methoxyphenyl, and CH₂CON-piperidine bearing Z¹,Z² substituents]

| X | Z¹,Z² | m.p. (°C.) | Molecular Formula | Elemental Anal. Calcd. (Found) | | |
|---|---|---|---|---|---|---|
| | | | | C | H | N |
| 5-Cl | =NOH | 209–211 | $C_{22}H_{22}ClN_3O_4$ | 61.75 (61.82 | 5.18 5.23 | 9.82 9.89) |
| 5-Cl | =O | 171–173 | $C_{22}H_{21}ClN_2O_4$ | 65.00 (64.11 | 5.13 5.21 | 6.79 6.68) |
| 5-NO₂ | –O–CH₂–CH₂–O– (dioxolane) | 197 | $C_{24}H_{25}ClN_3O_7$ | 61.66 (61.56 | 5.39 5.39 | 8.99 8.87) |
| H | –O–CH₂–CH₂–O– (dioxolane) | 164–166 | $C_{24}H_{26}N_2O_5$ | 68.23 (68.21 | 6.20 6.19 | 6.63 6.54) |
| 5-NO₂ | =O | 166–167 | $C_{22}H_{21}N_3O_6$ | 62.41 (62.72 | 5.00 5.05 | 9.92 9.84) |
| 5-NO₂ | =NOH | 199–200 | $C_{22}H_{22}N_4O_6$ | 60.27 (60.39 | 5.06 5.01 | 12.78 12.71) |
| 5-Cl | OH, H | 180–182 | $C_{22}H_{23}ClN_2O_4$ | 63.69 (63.12 | 5.59 5.53 | 6.75 6.71) |
| 5-NO₂ | OH, H | 204–205 | $C_{22}H_{23}N_3O_6$ | 62.11 (62.33 | 5.45 5.53 | 9.88 9.90) |

EXAMPLE 3

2-(7-Chloro-1,8-naphthyridin-2-yl)-3-(1,4-dioxa-8-azaspiro[4.5]decan-8-yl)carbonylmethylisoindolin-1-one To a mixture of 20.4 g of 2-(7-chloro-1,8-naphthyridin-2-yl)-3-oxoisoindoline-1-acetic acid and 250 ml of dimethylformamide were added 16 ml of triethylamine, 10.4 g of 1,4-dioxa-8-azaspiro[4.5]decane and 16 ml of diethyl phosphorocyanidate, and the mixture was stirred for 20 minutes. After addition of water, the resulting crystalline precipitate was collected by filtration, washed with water and dried to give 26.4 g of crude crystals. Recrystallization from methylene chloride-ethyl acetate gave 27.1 g of colorless crystals melting at 238°–239° C.

Elemental analysis: Calcd. for $C_{25}H_{23}ClN_4O_4$: C 62.70; H 4.84; N 11.70 Found: C 62.84; H 4.90; N 11.67.

EXAMPLE 4

In the same manner as Example 3, there were obtained the compounds listed in Table 4.

TABLE 4

[Structure: isoindolin-1-one with X substituent, N-substituted with 7-chloro-1,8-naphthyridin-2-yl, and CH₂CON-piperidine bearing Z¹,Z² substituents]

| X | Z¹,Z² | m.p. (°C.) | Molecular Formula | Elemental Anal. Calcd. (Found) | | |
|---|---|---|---|---|---|---|
| | | | | C | H | N |
| H | =NOH | 245–247 | $C_{23}H_{20}ClN_5O_3$ | 61.40 (61.15 | 4.48 4.49 | 15.57 15.31) |
| H | =O | 263 | $C_{23}H_{19}ClN_4O_3$ | 63.52 (63.64 | 4.40 4.46 | 12.88 12.33) |
| H | OCH₃, OCH₃ | 207–208 | $C_{25}H_{25}ClN_4O_4$ | 62.43 (62.66 | 5.24 5.19 | 11.65 11.77) |
| H | OC₂H₅, OC₂H₅ | 203–204 | $C_{27}H_{29}ClN_4O_4$ | 63.71 (63.94 | 5.74 5.57 | 11.01 11.13) |

TABLE 4-continued

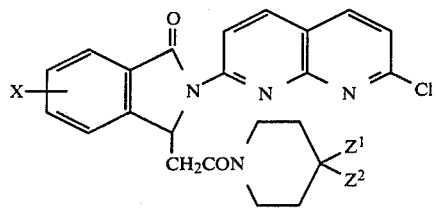

| X | $Z^1, Z^2$ | m.p. (°C.) | Molecular Formula | Elemental Anal. Calcd. (Found) | | |
|---|---|---|---|---|---|---|
| | | | | C | H | N |
| H | O-C(CH$_3$)$_2$-O (5-membered dioxolane with gem-dimethyl) | 218-221 | $C_{28}H_{29}ClN_4O_4$ | 64.55 (64.50 | 5.61 5.45 | 10.75 10.80) |
| H | O-(CH$_2$)$_3$-O (6-membered dioxane) | 281-282 | $C_{26}H_{25}ClN_4O_4$ | 63.35 (62.34 | 5.11 5.08 | 11.37 11.18) |
| H | S-(CH$_2$)$_3$-S (6-membered dithiane) | 225-227 | $C_{26}H_{25}ClN_4O_2S_2$ | 59.47 (59.40 | 4.80 4.76 | 10.67 10.63) |
| H | S-(CH$_2$)$_2$-S (5-membered dithiolane) | 249-250 | $C_{25}H_{23}ClN_4O_2S_2$ | 58.76 (58.65 | 4.54 4.46 | 10.96 10.86) |
| 5-Cl | =O | 259-260 | $C_{23}H_{18}Cl_2N_4O_3$ | 58.86 (58.43 | 3.87 3.85 | 11.94 11.51) |
| 5-NO$_2$ | =O | 290-292 | $C_{23}H_{18}ClN_5O_5$ | 57.57 (57.33 | 3.78 3.74 | 14.59 14.47) |
| 5-Cl | O-(CH$_2$)$_2$-O | 263-264 | $C_{25}H_{22}Cl_2N_4O_4$ | 58.49 (58.34 | 4.32 4.12 | 10.91 10.64) |
| 5-NO$_2$ | O-(CH$_2$)$_2$-O | 295-297 | $C_{25}H_{22}ClN_5O_6$ | 57.31 (57.21 | 4.23 4.16 | 13.37 13.40) |
| 6-NO$_2$ | O-(CH$_2$)$_2$-O | 295-297 | $C_{25}H_{22}ClN_5O_6$ | 57.31 (57.03 | 4.23 4.19 | 13.37 13.13) |
| H | OCOCH$_3$, H | 234-235 | $C_{25}H_{23}ClN_4O_4$ | 62.70 (62.99 | 4.84 4.73 | 11.70 11.87) |
| H | OCOC$_2$H$_5$, H | 233-234 | $C_{26}H_{25}ClN_4O_4$ | 63.35 (63.46 | 5.11 5.18 | 11.37 11.26) |
| 6-NO$_2$ | =O | >300 | $C_{23}H_{18}ClN_5O_5$ | 57.56 (57.50 | 3.78 3.35 | 14.60 14.41) |
| H | OH, H | 270-271 | $C_{23}H_{21}ClN_4O_3$ | 63.23 (63.00 | 4.84 4.78 | 12.82 12.72) |

EXAMPLE 5

2-(7-Chloro-5-methyl-1,8-naphthyridin-2-yl)-3-(1,4-dioxa-8-azaspiro[4.5]decan-8-yl)carbonylmethylisoindolin-1-one With ice-cooling and stirring, 1.6 g of 1,4-dioxa-8-azaspiro[4.5]decane, 2 ml of triethylamine and 2.2 g of diethyl phosphorocyanidate were successively added to a solution of 3.5 g of 2-(7-chloro-5-methyl-1,8-naphthyridin-2-yl)-3-oxoisoindoline-1-acetic acid in 30 ml of dimethylformamide. The mixture was stirred with ice-cooling for an additional 2 hours and 200 ml of ice-water was added thereto. The mixture was allowed to stand, and the resulting crystalline precipitate was collected by filtration, washed with water and dried. Recrystallization from dichloromethane-ether (1:4) gave 4.23 g of colorless crystals melting at 259°–262° C.

Elemental analysis: Calcd. for $C_{26}H_{25}ClN_4O_4$: C 63.34; H 5.11; N 11.37 Found: C 63.39; H 5.10; N 11.41.

EXAMPLE 6

2-(7-Chloro-5-methyl-1,8-naphthyridin-2-yl)-3-(4-piperidon-1-yl)carbonylmethylisoindolin-1-one With ice-cooling and stirring, 1.2 g of 4-piperidone, 1.5 ml of triethylamine, 0.5 g of 4-dimethylaminopyridine and 1.6 g of diethyl phosphorocyanidate were successively added to a solution of 2.1 g of 2-(7-chloro-5-methyl-1,8-naphthyridin-2-yl)-3-oxoisoindoline-1-acetic acid in 35 ml of dimethylformamide. After stirring with ice-cooling for an additional 3 hours, 200 ml of ice water was added, and the resulting crystalline precipitate was collected by filtration, washed with water and dried. Recrystallization from dichloromethane gave 2.13 g of colorless crystals melting at 312°–314° C.

Elemental analysis: Calcd. for $C_{24}H_{21}ClN_4O_3$: C 64.21; H 4.72; N 12.48 Found: C 64.33; H 4.69; N 12.60.

EXAMPLE 7

2-(7-Chloro-1,8-naphthyridin-2-yl)-3-(1,4-dioxa-8-azaspiro[4.5]decan-8-yl)carbonylmethylisoindolin-1-one (1) To 2.6 g of 2-(7-chloro-1,8-naphthyridin-2-yl)-3-oxoisoindoline-1-acetic acid was added 6 ml of thionyl chloride. The mixture was stirred at room temperature for 30 minutes and then heated at 60° C. for 15 minutes. Removal of the excess thionyl chloride by distillation gave 2.66 of 2-(7-chloro-1,8-naphthyridin-2-yl)-3-oxoisoindoline-1-acetyl chloride. This product was directly submitted to the next step without purification.

(2) A solution of 2.66 g of the acetyl chloride derivative obtained by the above procedure in 20 ml of dichloromethane was added to a solution of 2.1 g of 1,4-dioxa-8-azaspiro[4.5]decane and 3 ml of triethylamine in 30 ml of dichloromethane with ice-cooling and stirring. After stirring with ice-cooling for 30 minutes, 300 ml of water was added and the dichloromethane layer was separated, washed with water and dried on anhydrous magnesium sulfate. Removal of the solvent by distillation gave 2.71 g of crude crystals. This product was recrystallized from methylene chloride-ether (1:2) to give the same compound as that obtained in Example 2. It melted at 238°–239° C.

FORMULATION EXAMPLE 1

| | |
|---|---|
| (1) 2-(7-Chloro-1,8-naphthyridin-2-yl)-3-(1,4-dioxa-8-azaspiro[4.5]decan-8-yl)carbonylmethylisoindolin-1-one | 1 g |
| (2) Lactose | 89 g |
| (3) Corn starch | 29 g |
| (4) Magnesium stearate | 1 g |

The above ingredients (1) and (2) and 15 g of corn starch were mixed and granulated with a paste prepared from 8 g of corn starch. To the granules were added 6 g of corn starch and ingredient (4), and the mixture is compressed on a tableting machine to give 1000 tablets of 5 mm diameter each containing 1 mg of ingredient (1).

REFERENCE EXAMPLE 1

2-(7-Chloro-1,8-naphthyridin-2-yl)-3-oxoisoindoline-1-acetic acid (1) A mixture of 46.0 g of 2-(7-chloro-1,8-naphthyridin-2-yl)-3-hydroxyisoindolin-1-one, 78 g of t-butyloxycarbonylmethylenetriphenylphosphorane and 800 ml of toluene was refluxed for 5 hours. The mixture was concentrated and the residue was purified by silica gel column chromatography (dichloromethane-ethyl acetate) to give 54.5 g of t-butyl 2-(7-chloro-1,8-naphthyridin-2-yl)-3-oxoisoindoline-1-acetate. Recrystallization from toluene-ether gave colorless crystals melting at 210°–211° C.

Elemental analysis: Calcd. for $C_{22}H_{20}ClN_3O_3$: C 64.47; H 4.92; N 10.25 Found: C 64.66; H 4.87; N 10.27.

(2) In 270 ml of trifluoroacetic acid was dissolved 54.5 g of the t-butyl ester obtained in the above. The solution was allowed to stand for 2 hours and then concentrated, followed by addition of ether. The resulting crystalline precipitate was collected by filtration to give 47.0 g of crystals melting at 225°–226° C.

Elemental analysis: Calcd. for $C_{18}H_{12}ClN_3O_3$: C 61.11; H 3.42; N 11.88 Found: C 61.30; H 3.46; N 11.82.

REFERENCE EXAMPLE 2

6-Chloro-2-(4-methoxyphenyl)-3-oxoisoindoline-1-acetic acid (1) A solution of 20 g of 5-chloro-2-(4-methoxyphenyl)-3-hydroxyisoindolin-1-one and 27 g of ethoxycarbonylmethylenetriphenylphosphorane in 200 ml of dry toluene was heated at 110° C. for 3 hours. After cooling, the resulting triphenylphosphine oxide was removed. Recrystallization of the crude crystals gave 19.6 g of ethyl 6-chloro-2-(4-methoxyphenyl-3-oxoisoindoline-1-acetate as colorless crystals melting at 129°–131° C.

Elemental analysis: Calcd. for $C_{19}H_{18}ClNO_4$: C 63.42; H 5.04; N 3.89 Found: C 63.47; H 5.06; N 3.87.

(2) To a solution of 16 g of the ester compound obtained by the above procedure (1) in 200 ml of methanol were added 50 ml of water and 27 g of potassium carbonate. The mixture was stirred at 80° C. for 3 hours. After cooling, the excess methanol was distilled off and 150 ml of 3N hydrochloric acid was added to the residue. The resulting crystalline precipitate was collected by filtration, washed with water, dried and recrystallized from methanol to give 14.2 g of the title compound melting at 250°–251° C.

Elemental analysis: Calcd. for $C_{17}H_{14}ClNO_4$: C 61.54; H 4.25; H 4.22 Found: C 61.53; H 4.26; N 4.30.

What is claimed is:

1. A compound of the formula

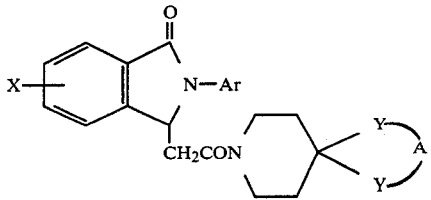

wherein X is hydrogen, halogen or nitro; Ar is phenyl, naphthyridinyl, or substituted phenyl or naphthyridinyl having one or two substituents of the class consisting of halogen, hydroxy, $C_{1-4}$ alkyl, $C_{1-4}$ alkoxy, nitro, amino, methylenedioxy, phenoxy, benzyloxy, $C_{2-5}$ alkanoyloxy, α- or ω-hydroxy-$C_{1-4}$ alkyl, benzoyl, amido, cyano, trifluoromethyl, $C_{1-4}$ alkylthio, $C_{2-5}$ alkanoyloxy-$C_{1-3}$ alkyl, $C_{2-5}$ alkanoylamino and $C_{1-4}$ alkoxycarbonyl; Y is oxygen or sulfur; and A is a $C_{2-4}$ alkylene chain or a $C_{2-4}$ alkylene chain having one or more $C_{1-4}$ alkyl side chains; or a physiologically acceptable acid addition salt thereof.

2. A compound according to claim 1, wherein Ar is phenyl.

3. A compound according to claim 1, wherein Ar is naphthyridinyl.

4. A compound according to claim 2, wherein the phenyl is substituted by $C_{1-4}$ alkoxy.

5. A compound according to claim 3, wherein the naphthyridinyl is substituted by halogen, $C_{1-4}$ alkyl, or both.

6. A compound according to claim 1, wherein X is hydrogen.

7. A compound according to claim 1, wherein Y is oxygen.

8. A compound according to claim 1, wherein X is hydrogen, Ar is naphthyridinyl that is substituted by halogen, Y is oxygen and A is an unbranched $C_{2-4}$ alkylene chain.

9. A compound according to claim 8, wherein A is ethylene.

10. The compound according to claim 1 that is 2-(7-chloro-1,8-naphthyridin-2-yl)-3-(1,5-dithia-9-azaspiro[5.5]undecan-9-yl)carbonylmethylisoindolin-1-one.

11. The compound according to claim 1 that is 2-(7-chloro-1,8-naphthyridin-2-yl)-3-(1,4-dioxa-8-azaspiro[4.5]decan-8-yl)carbonylmethylisoindolin-1-one.

12. A pharmaceutical composition suitable for prevention or treatment of psychosomatic diseases or anxiety neuroses that contains an amount of a compound according to claim 1 effective for prevention or treatment of said diseases or neuroses and a pharmaceutically acceptable carrier, vehicle or diluent therefor.

13. A method for prevention or treatment of psychosomatic diseases or anxiety neuroses in a mammal that comprises administering to said mammal an amount of a compound according to claim 1 that is effective for prevention or treatment of said diseases or neuroses.

14. A method for prevention or treatment of psychosomatic diseases or anxiety neuroses in a mammal that comprises administering to said mammal an amount of a pharmaceutical composition according to claim 12 that is effective for prevention or treatment of said diseases or neuroses.

* * * * *